United States Patent
Wang et al.

(10) Patent No.: US 12,171,736 B2
(45) Date of Patent: *Dec. 24, 2024

(54) COMPOSITIONS AND METHODS FOR PROMOTING GLYCOGEN SYNTHASE ACTIVITY AND AUGMENTING GLYCOGEN STORAGE CAPABILITY

(71) Applicant: NANJING NUTRABUILDING BIO-TECH CO., LTD., Nanjing (CN)

(72) Inventors: Mingru Wang, Nanjing (CN); Ronghua Yi, Nanjing (CN); Kylin Liao, Nanjing (CN); Wenbin Yu, Nanjing (CN)

(73) Assignee: NANJING NUTRABUILDING BIO-TECH CO., LTD., Nanjing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/483,630

(22) Filed: Oct. 10, 2023

(65) Prior Publication Data

US 2024/0041809 A1 Feb. 8, 2024

Related U.S. Application Data

(63) Continuation of application No. PCT/CN2022/086514, filed on Apr. 13, 2022.

(51) Int. Cl.
*A61K 31/197* (2006.01)
*A61P 21/00* (2006.01)

(52) U.S. Cl.
CPC ........... *A61K 31/197* (2013.01); *A61P 21/00* (2018.01)

(58) Field of Classification Search
CPC ........ A23L 33/10; A61K 31/197; A61P 21/00
See application file for complete search history.

(56) References Cited

U.S. PATENT DOCUMENTS

2006/0167098 A1* 7/2006 Fromenty ............ A23L 33/175
514/561
2022/0054441 A1* 2/2022 Liao .................... A61K 31/197

FOREIGN PATENT DOCUMENTS

WO 2004091598 A1 10/2004

OTHER PUBLICATIONS

Adeva-Andany (BBA clinical 5 (2016) 85-100) (Year: 2016).*
Arnaud Baquet et al., "Comparison of the effects of various amino acids on glycogen synthesis, lipogenesis and ketogenesis in isolated rat hepatocytes", Biochem.J.1991, vol. 273, pp. 57-62.
World Intellectual Property Organization (WIPO) International Search Report for PCT/CN2022/086514 Jul. 8, 2022, 2022 6 pages.

(Continued)

*Primary Examiner* — Savitha M Rao
(74) *Attorney, Agent, or Firm* — ANOVA LAW GROUP, PLLC

(57) ABSTRACT

The present invention provides compositions and methods for promoting glycogen synthase activity and augmenting glycogen storage capability in muscle tissue and/or liver tissue in a mammal, relating to administration to the mammal of an effective amount of β-aminoisobutyric acid (BAIBA), an analog or derivative thereof, or a pharmaceutically acceptable salt, ester, acid, polymer, analog or derivative thereof.

14 Claims, 2 Drawing Sheets

*Effect of BAIBA on hepatic glycogen content*

($^\#P < 0.05$, $^{\#\#}P < 0.01$, vs Exercise Group)

(56) References Cited

OTHER PUBLICATIONS

Arnaud Baquet et al. "Comparison of the effects of various amino acids on glycogen 1-23 synthesis, lipogenesis and ketogenesis in isolated rat hepatocytes" Biochem.J., vol. 273, Dec. 31, 1991 (Dec. 31, 1991), pp. 57-62.

Lee D. Roberts et al. "β Aminoisobutyric Acid Induces Browning of White Fat and Hepatic β oxidation and is Inversely Correlated with Cardiometabolic Risk Factors", Cell Metab., vol. 19, No. 01, Jan. 7, 2014 (Jan. 7, 2014), pp. 96-108(pp. 1-32).

Yukiko Kitase et al. aminoisobutyric Acid, L-BAIBA, Is a Muscle-Derived Osteocyte Survival Factor, Cell Rep., vol. 22, No. 06, Feb. 6, 2018 (Feb. 6, 2018), pp. 1531-1544(pp. 1-29).

Dmitrii A. et al. "Beta-Aminoisobutyric Acid as a Novel Regulator of Carbohydrate and Lipid Metabolism", Nutrients, vol. 11, Feb. 28, 2019 (Feb. 28, 2019). pp. 1-15.

\* cited by examiner

*Effect of BAIBA on hepatic glycogen content*

(#P <0.05, ##P <0.01, vs Exercise Group)

*Effect of BAIBA on hepatic glycogen synthetase content*

*Effect of BAIBA on muscle glycogen content*

($^\#P < 0.05, ^{\#\#}P < 0.01$, vs Exercise Group=

*Effect of BAIBA on muscle glycogen synthetase content*

($^\#P < 0.05, ^{\#\#}P < 0.01$, vs Exercise Group)

COMPOSITIONS AND METHODS FOR PROMOTING GLYCOGEN SYNTHASE ACTIVITY AND AUGMENTING GLYCOGEN STORAGE CAPABILITY

CROSS-REFERENCE TO RELATED APPLICATION

This Application is a continuation application of international patent Application No. PCT/CN2022/086514, filed on Apr. 13, 2022, which claims the priority of the international Application PCT/CN2021/087159, filed on Apr. 14, 2021, the disclosures of which are incorporated herein by reference in their entirety.

FIELD OF THE DISCLOSURE

The present disclosure generally relates to the field of health food and dietary supplements and, more particularly, relates to compositions and methods for promoting glycogen synthase activity and augmenting glycogen storage capability.

BACKGROUND

Muscle glycogen is a main fuel source of skeletal muscle tissue during prolonged strenuous exercise, such as weightlifting, weightlifting, strongman and competitive fitness, and other sports training. It has been proven that low level of muscle glycogen is a key physiological factor that not only can lead to increased fatigue (e.g., increased fatigue during strenuous exercise), but also plays a role in maintaining strict anaerobic exercise capacity. As such, muscle glycogen is generally considered as the preferred source of energy for all our muscles. On the other hand, insufficient muscle glycogen is likely to inhibit various body functions.

Optimizing liver and muscle glycogen storage is the goal of many athletes who want to maximize their athletic ability, especially those who participate in sports that require a burst of powerful energy in a short period (e.g., weightlifting and sprinting), and those who repeat high-intensity sports for a long time. The accepted method for maximizing the acceptance of muscle glycogen content is through "carbohydrate (CHO) loading", which usually involves depleting muscle glycogen reserves through prolonged submaximal exercise (>90 minutes) and then eating a high CHO diet (>70% of calories CHO) for several days. Using this method can replenish the muscle glycogen content to a habitual resting level within 24 hours, and super-compensate more than 100% of the reserve within 48-72 hours. In addition to this traditional method of supplementing high CHO to increase muscle glycogen storage, researchers have found that use of certain dietary supplements could promote muscle glycogen storage. In 2000, Nelson et al. reported that creatine supplementation before exercise could enhance the muscle glycogen supercompensation. See Nelson, A. G., et al., *Muscle glycogen supercompensation is enhanced by prior creatine supplementation*. Medicine and science in sports and exercise, 2001. 33(7): p. 1096-1100. In 2016, Roberts et al. reported a greater increase in postexercise muscle glycogen storage following creatine supplementation in addition to a high-CHO diet. See Roberts, P. A., et al., *Creatine ingestion augments dietary carbohydrate mediated muscle glycogen supercompensation during the initial 24 h of recovery following prolonged exhaustive exercise in humans*. Amino acids, 2016. 48(8): p. 1831-1842. As such, it is promising to identify some factors that enhance the rate of synthesis of glycogen storage in a limited time frame, improve glycogen storage from a limited CHO intake, or increase muscle glycogen supercompensation.

β-aminoisobutyric acid (BAIBA) is a non-protein amino acid secreted by skeletal muscles upon regular exercise via peroxisome proliferator-activated receptor gamma coactivator 1-alpha (PGC-1)-dependent mechanism. There are two enantiomers of BAIBA in biological systems: D-BAIBA and L-BAIBA. L-BAIBA is generated from catabolic reactions of branched-chain amino acid L-valine, and D-BAIBA is produced in the cytosol from thymine in a metabolic pathway. See, e.g., Tanianskii, D. A., et al., *Beta-Aminoisobutyric Acid as a Novel Regulator of Carbohydrate and Lipid Metabolism*. Nutrients, 2019. 11(3). BAIBA has been discovered as a novel endogenous protective myokine regulating adipose tissue browning, improving insulin sensitivity, and protecting against high-fat diet-induced obesity. It has been reported that BAIBA may decrease body fat mass, improve glucose tolerance and insulin sensitivity in mice without changing food intake.

Further studies for the application of BAIBA and associated functions are needed. In the present application, novel compositions and methods have been found by administrating an effective amount of BAIBA, an analog or derivative thereof, or a pharmaceutically acceptable salt, ester, acid, polymer, analog or derivative thereof, to promote glycogen synthase activity and/or augment glycogen storage capability, particularly in muscle tissue and/or liver tissue.

SUMMARY

This summary is provided to introduce a selection of concepts in a simplified form that is further described below in the Detailed Description. This summary is not intended to identify key features or essential features of the claimed subject matter, nor is it intended to be used to limit the scope of the claimed subject matter.

The present invention generally relates to compositions and methods for promoting glycogen synthase activity and/or augmenting glycogen storage capability, particularly in muscle tissue and/or liver tissue. In particular, the present invention relates to administration of compositions (e.g., supplements) comprising an effective amount of β-aminoisobutyric acid (BAIBA), an analog or derivative thereof, or a pharmaceutically acceptable salt, ester, acid, polymer, analog or derivative thereof. For instance, BAIBA supplementation was found to promote glycogen synthase activity, and administration of β-aminoisobutyric acid supplementation (e.g., daily for a period pre- and/or post-exercise) is able to augment dietary carbohydrate mediated muscle glycogen supercompensation.

One aspect of this invention relates to method for promoting glycogen synthase activity and/or augmenting glycogen storage capability in muscle tissue and/or liver tissue of a mammal (e.g., human or an animal), comprising administrating to the mammal a therapeutically effective amount of β-aminoisobutyric acid (BAIBA), an analog or derivative thereof, or a pharmaceutically acceptable salt, ester, acid, polymer, analog or derivative thereof.

In some embodiments, BAIBA is administrated as a dietary supplement. In some embodiments, BAIBA is administrated orally or by injection.

In some embodiments, supplementing BAIBA promotes the glycogen synthase activity and augments glycogen storage capability.

In some embodiments, BAIBA is administered to promote the liver glycogen synthase activity and augment liver glycogen storage capability In some embodiments, BAIBA is administered before exercise and capable of augmenting dietary carbohydrate-mediated muscle glycogen supercompensation before the exercise.

In some embodiments, BAIBA is administered after exercise and capable of augmenting dietary carbohydrate-mediated muscle glycogen supercompensation after the exercise.

Examples of exercise include but are not limited to long-duration endurance training, resistance training, and a combination thereof.

In some embodiments, BAIBA comprises L-BAIBA, D-BAIBA, or a combination thereof.

In some embodiments, BAIBA is administered at a dose ranging from about 20 to about 2000 mg/day.

In some embodiments, BAIBA is administered for at least 3-14 days.

Still in some embodiments, BAIBA is administered in a form of aqueous solution, aqueous suspension, capsule, drop, granule, liquid, powder, syrup, tablet, functionalized food, beverage, toothpaste, or sublingual articles. In some embodiments, the mammal comprises a human.

In another aspect, the present invention provides a composition for promoting glycogen synthase activity and/or augmenting glycogen storage capability in muscle tissue and/or liver tissue of a mammal, comprising a therapeutically effective amount of β-aminoisobutyric acid (BAIBA), an analog or derivative thereof, or a pharmaceutically acceptable salt, ester, acid, polymer, analog or derivative thereof.

In some embodiments, the composition comprises a dose of BAIBA, wherein the dose of BAIBA ranges from about 20 to about 2000 mg/day.

In some embodiments, the composition is to be administrated to the mammal as a supplement. In some embodiments, the composition is administered to the mammal orally or by injection.

In some embodiments, supplementing BAIBA promotes the glycogen synthase activity and augments glycogen storage capability.

In some embodiments, BAIBA is administered to promote the liver glycogen synthase activity and augment liver glycogen storage capability.

In some embodiments, the composition is administered before exercise and capable of augmenting dietary carbohydrate-mediated muscle glycogen supercompensation before the exercise. In some embodiments, the composition is administrated after exercise and capable of augmenting dietary carbohydrate-mediated muscle glycogen supercompensation after the exercise. Examples of exercise include, but are not limited to, long-duration endurance training, resistance training, and a combination thereof.

In some embodiments, BAIBA comprises L-BAIBA, D-BAIBA, or a combination thereof.

In some embodiments, the composition is to be administrated for at least 3-14 days.

In some embodiments, the composition is in a form of aqueous solution, aqueous suspension, capsule, drop, granule, liquid, powder, syrup, tablet, functionalized food, beverage, toothpaste, or sublingual articles.

In some embodiments, the mammal comprises a human.

As used herein, the term "or" is meant to include both "and" and "or." In other words, the term "or" may also be replaced with "and/or."

As used herein, the term "therapeutically effective amount," which can be interchanged with "physiologically effective amount," means an amount that is required to provide or result in effect in therapy or physiological conditioning, or an amount sufficient to provide a therapeutic or physiological effect. An amount that is effective in therapy or physiological conditioning is an amount which produces a biological activity (or physiological response) and will depend, among other things, on the individual.

As used herein, the term "pharmaceutically acceptable,"" which can be interchanged with "physiologically acceptable," means that which is useful in preparing a pharmaceutical or physiological composition (e.g., a supplement) is generally safe, non-toxic and neither biologically nor otherwise undesirable and includes that which is acceptable for veterinary uses or human pharmaceutical use.

Unless otherwise specifically indicated, the technical and scientific terms used in the framework of the present invention have generally accepted meanings known to those skilled in the art to which the invention relates. In the text of the description and claims, the singular also includes plural references, unless the context clearly dictates otherwise. As used herein, the singular forms "a," "an" and "the" are intended to include the plural forms as well, unless the context clearly indicates otherwise.

BRIEF DESCRIPTIONS OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DETAILED DESCRIPTION

Figure 1:
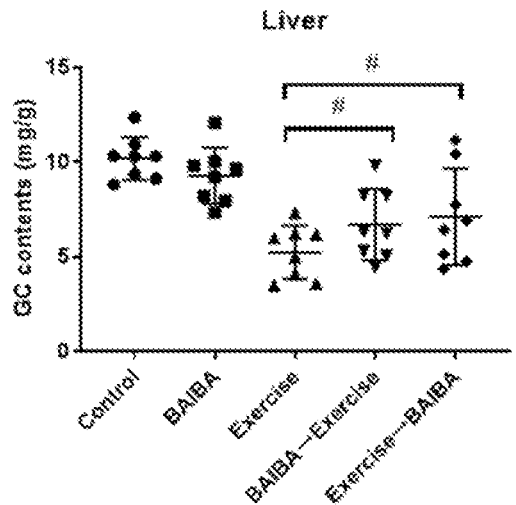
FIG. 1 shows test results related to effect of BAIBA on hepatic glycogen content.

Reference will now be made in detail to the preferred embodiments of the invention, examples of which are further illustrated. While the invention will be described in conjunction with the preferred embodiments, it will be understood that they are not intended to limit the invention to these embodiments. To the contrary, the invention is intended to cover alternatives, modifications and equivalents, which may be included within the spirit and scope of the invention as defined by the claims. Furthermore, in the detailed description of the present invention, numerous specific details are set forth in order to provide a thorough understanding of the present invention. However, it will be obvious to one of ordinary skill in the art that the present invention may be practiced without these specific details. In other instances, well known methods, procedures, components, and other features have not been described in detail as not to unnecessarily obscure aspects of the present invention.

Generally speaking, various embodiments of the present invention provide for methods comprising administrating to a mammal (e.g., human or an animal) an effective amount of β-aminoisobutyric acid (BAIBA) (e.g., L-BAIBA and/or D-BAIBA), an analog or derivative thereof, or a pharmaceutically acceptable salt, ester, acid, polymer, analog or derivative thereof (e.g., at a daily dose ranging from about 20 to about 2000 mg/day for a period, such as at least 3-14 days), in order to promote glycogen synthase activity and/or augment glycogen storage capability in muscle tissue and/or liver tissue of the mammal. Particularly, administration of BAIBA supplement (e.g., daily for a period pre- and/or post-exercise) was surprisingly found to augment dietary carbohydrate mediated muscle glycogen supercompensation. BAIBA may be administrated in a variety of forms (e.g., orally or by injection), such as aqueous solution, aqueous suspension, capsule, drop, granule, liquid, powder, syrup, tablet, functionalized food, beverage, toothpaste, or sublingual articles. The present invention also provides compositions for promoting glycogen synthase activity and/or augmenting glycogen storage capability in muscle tissue and/or liver tissue, including an effective amount of BAIBA, an analog or derivative thereof, or a pharmaceutically acceptable salt, ester, acid, polymer, analog or derivative thereof (e.g., with a particular dose of BAIBA).

The following examples are illustrative of select embodiments of the present invention and are not meant to limit the scope of the invention.

Example 1 Effect of BAIBA on Liver and Skeletal Muscle Glycogen Levels in Obese Mice Post quarantine, animals were acclimatized for one week and subsequently the animals were randomized based on body weight stratification. Initially, mice were allocated broadly into two groups with one group receiving the Normal Diet (ND) representing normal subjects and the other receiving a defined High Fat Diet (HFD) representing obese subjects. The HFD was a defined lard-based diet procured from Research Diets, New Jersey, USA (Product No.— D12492, with 60 Kcal % from fat, 20 Kcal % from proteins, and 20 Kcal % from carbohydrates; Lot no. 20050105 and expiry date 30 Nov. 2020). The ND was a defined control diet procured from Hylasco Biotechnology Pvt. Ltd, manufactured by PMI Nutrition International (Batch no. MAY06202 and expiry date February 2021) containing similar nutrients as HFD but with 13 Kcal % from fat, 17 Kcal % from proteins, and 20 Kcal % from carbohydrates.

The mice in the respective groups were put on ND and HFD for 8 weeks starting at age of ~8 weeks. Food was offered twice a week by replacing the left-over feed with fresh feed and total weekly feed consumption was calculated and expressed as g feed/day/animal. Bodyweight was recorded once a week. At the end of 8 weeks (Day 57), mean body weight was measured, and animals were randomized based on body weight stratification and grouped separately into respective ND and HFD groups shown in the following experimental design. After the feeding/induction period (Week 1 to 8), the treatment period was from Week 9 to Week 16. A total of 36 mice were randomly grouped into six groups with n=6 in each group. Control Group: Normal mice, maintained on normal diet for 8 weeks, receiving neither exercise nor L-BAIBA treatment. Model Group: Obese mice, maintained on HFD for 8 weeks, receiving neither exercise nor L-BAIBA treatment. Exercise Group: Obese mice, maintained on HFD for 8 weeks, receiving only exercise and no L-BAIBA treatment. BAIBA Group: Obese mice, maintained on HFD for 8 weeks, receiving only LBAIBA treatment and no exercise. Exercise+BAIBA Group: Obese mice, maintained on HFD for 8 weeks, receiving L-BAIBA treatment and exercise.

A regular treadmill (PowerMax) used by humans was availed for subjecting mice to daily exercise. A special lane box made of Perspex was used to fabricate the treadmill's running platform, forming a modified 6-lane rodent treadmill allowing 6 animals to run simultaneously. The mice in the specified groups were exercised daily throughout the treatment period (week 9-16). Exercise consisted of treadmill running at a speed 3.0 m/min with no inclination of the treadmill. Mice were allowed to freely explore the treadmill until each mouse had explored its lane and the treadmill was turned on with a slow increase in the speed until animals begin running at set speed. During the first week of the treatment period, as an introduction the mice were forced to running exercise for 8 minutes. Subsequently, the exercise duration was increased to 9 minutes during the following week. The exercise duration was finally set to 10 minutes daily for the rest of weeks. Exercise took place in a room separated from the actual housing room to which all mice were transferred and kept during the exercise procedures in order to minimize environmental confounders among the mice not subjected to the exercise protocol. Before exercise, animals were observed for normal health status and after exercise they were returned to their respective cages. Entire procedure was supervised by study personnel and no abnormal behavior of animals was observed. Forced treadmill exercise was carried out at preferred lux and noise free conditions.

After completion of 8 weeks of experimentation (at the end of treatment on the day 114), animals were euthanized using an overdose of isoflurane (20% v/v in propylene glycol in a glass vacuum desiccator). The whole soleus muscle tissues and a sample of the main lobe of the liver were used to measure glycogen content using a modified protocol described in Methods in Enzymology Vol. III (Colowick and Kaplan, 1957).

Results are presented in following Table 1. Compared to animals maintained on normal diet, HFD animals showed a reduction in glycogen levels in both liver and muscle tissues as compared between the Model group and Control Group. In the other HFD groups, mice subjected to L-BAIBA administration alone and a combination of L-BAIBA and exercise resulted in a significant increase in both hepatic and muscle glycogen levels. This effect was better than the corresponding glycogen levels observed in the HFD group subjected to exercise alone. It was clearly shown that administration of L-BAIBA improves glycogen synthesis and storage in liver and skeletal muscle through its effects on glucose homeostasis in obese animals.

TABLE 1

Effect of oral BAIBA administration on liver and skeletal muscle glycogen levels.

| Group | Liver glycogen (mg/g tissue) | Muscle glycogen (mg/g tissue) |
| --- | --- | --- |
| Control Group | 7.86 ± 0.59# | 0.14 ± 0.01# |
| Model Group | 6.56 ± 0.22 | 0.02 ± 0.01 |
| Exercise Group | 7.87 ± 0.85# | 0.13 ± 0.03# |
| BAIBA Group | 9.66 ± 1.19# | 0.31 ± 0.06# |
| Exercise + BAIBA Group | 9.95 ± 0.61# | 0.29 ± 0.08# |

P < 0.05, vs Model.

Example 2 Effect of BAIBA on Liver and Skeletal Muscle Glycogen Levels in Normal Mice SPF-grade male C57 mice (8 weeks old) were purchased from Nanjing Qinglongshan Laboratory Animal Breeding Center. Mice were housed individually in a steel cage in a room at 24° C. with a 12:12 h (Light: Dark) photoperiod and standard diet. Food and water were provided ad libitum. Forty mice were randomly divided into five groups. Control Group: Receiving neither exercise nor L-BAIBA treatment. Exercise Group: Receiving only exercise and no L-BAIBA treatment. BAIBA Group: Receiving only L-BAIBA treatment and no exercise. Pre-workout Group: Receiving L-BAIBA treatment before exercise. Post-workout Group: Receiving L-BAIBA treatment after exercise. Samples were administered orally (gavage volume was 0.1 mL/10 g per mouse) via a gavage tube for 2 weeks.

The exercise consisted of treadmill running at a speed of 3.0 m/min with no inclination of the treadmill. Mice were allowed to freely explore the treadmill until each mouse had explored its lane and the treadmill was turned on with a slow increase in the speed until animals begin running at set speed. During the first week of the treatment period, as an introduction the mice were forced to running exercise for 8 minutes. Subsequently, the exercise duration was increased to 9 minutes during the following week. The exercise duration was finally set to 10 minutes daily for the rest of weeks.

After 30 minutes of exercise on day 14th, mice were injected with 0.1 to 0.3 mL 1% thiopental sodium intraperitoneally in order to general anesthesia. The soleus of the hind limbs of mice and liver were taken to detect the content of glycogen contents and glycogen synthetase with ELISA Kits.

Figure 2:
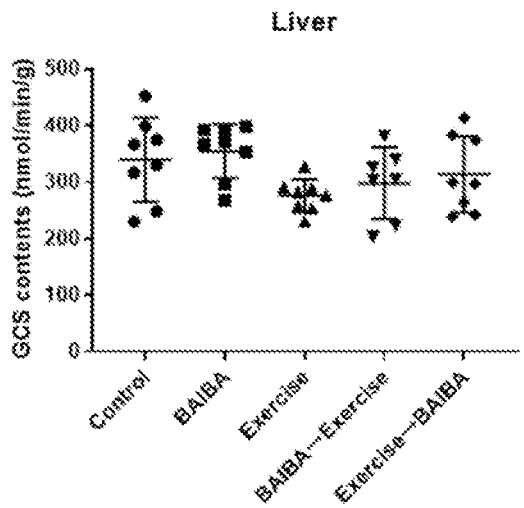
FIG. 2 shows test results related to effect of BAIBA on hepatic glycogen synthetase content.
Figure 3:
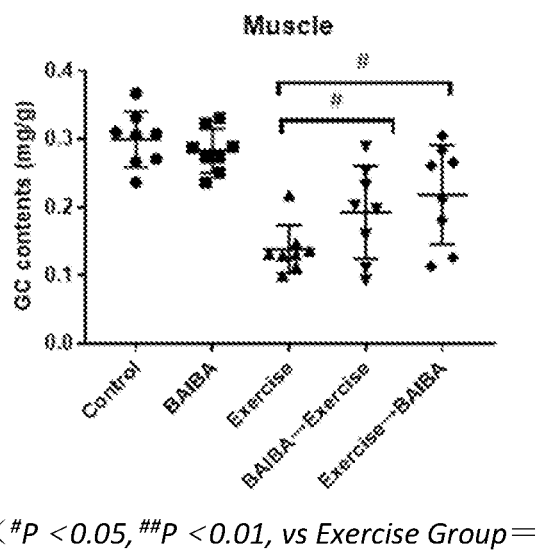
FIG. 3 shows test results related to effect of BAIBA on muscle glycogen content.
Figure 4:
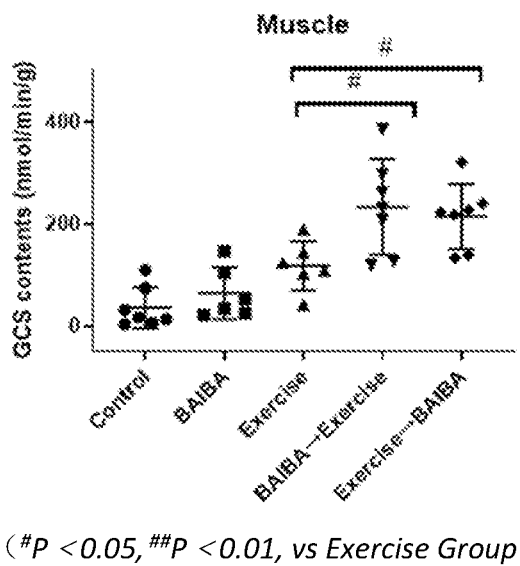
FIG. 4 shows test results related to effect of BAIBA on muscle glycogen synthetase content.

Results are shown in FIGS. 1-4. More specifically, FIG. 1 illustrates effect of BAIBA on hepatic glycogen content. FIG. 2 illustrates effect of BAIBA on hepatic glycogen synthetase content. FIG. 3 illustrates effect of BAIBA on muscle glycogen content. FIG. 4 illustrates effect of BAIBA on muscle glycogen synthetase content. Compared to Exercise group animals, Pre-workout and Post-work group animals showed an increase in glycogen levels in both liver and muscle tissues. Also, mice subjected to L-BAIBA administration also resulted in a significant increase in muscle glycogen synthetase content. It was clearly shown that administration of L-BAIBA improves glycogen synthesis and storage in liver and skeletal muscle.

Notably, in the tests described above, muscle biopsy was used for glycogen content testing, glycogen synthase activity testing and L-BAIBA levels, etc. To avoid potential confounding metabolic effects arising from multiple biopsy sampling throughout the study, biopsy sites were separated by at least 2.5 cm.

Although specific embodiments and examples of this invention have been illustrated herein, it will be appreciated by those skilled in the art that any modifications and variations can be made without departing from the spirit of the invention. The examples and illustrations above are not intended to limit the scope of this invention. Any combination of embodiments of this invention, along with any obvious their extension or analogs, are within the scope of this invention. Further, it is intended that this invention encompass any arrangement, which is calculated to achieve that same purpose, and all such variations and modifications as fall within the scope of the appended claims.

All the features disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example of a generic series of equivalent or similar features.

OTHER EMBODIMENTS

It is to be understood that while the invention has been described in conjunction with the detailed description thereof and accompanying figures, the foregoing description and accompanying figures are only intended to illustrate, and not limit the scope of the invention, which is defined by the scope of the appended claims. Other aspects, advantages, and modifications are within the scope of the following claims. All publications referenced herein are incorporated by reference in their entireties.

What is claimed is:

1. A method for promoting glycogen synthase activity and/or augmenting glycogen storage capability in muscle tissue and/or liver tissue of a mammal, comprising administrating to the mammal a therapeutically effective amount of β-aminoisobutyric acid (BAIBA), or a pharmaceutically acceptable salt, ester, or acid thereof, wherein BAIBA is administrated at a dose ranging from about 20 mg/day to about 2000 mg/day, is administrated orally pre-exercise, and is capable of augmenting dietary carbohydrate-mediated muscle glycogen supercompensation after a predefined number of days of pre-exercise administration.

2. The method of claim 1, wherein BAIBA is administrated as a dietary supplement.

3. The method of claim 1, wherein BAIBA is administrated to promote the liver glycogen synthase activity and augment liver glycogen storage capability.

4. The method of claim 1, wherein the exercise comprises long-duration endurance training, resistance training, or a combination thereof.

5. A method for promoting glycogen synthase activity and/or augmenting glycogen storage capability in muscle tissue and/or liver tissue of a mammal, comprising administrating to the mammal a therapeutically effective amount of β-aminoisobutyric acid (BAIBA), or a pharmaceutically acceptable salt, ester, or acid thereof, wherein BAIBA is administrated at a dose ranging from about 20 mg/day to about 2000 mg/day, is administrated orally after exercise, and is capable of augmenting dietary carbohydrate-mediated muscle glycogen supercompensation after a predefined number of days of after-exercise administration.

6. The method of claim 5, wherein the exercise comprises long-duration endurance training, resistance training, or a combination thereof.

7. The method of claim 1, wherein BAIBA comprises L-BAIBA, D-BAIBA, or a combination thereof.

8. The method of claim 1, wherein BAIBA is administrated in a form of capsule, granule, powder, tablet, functionalized food, toothpaste, or sublingual articles.

9. The method of claim 5, wherein BAIBA is administrated as a dietary supplement.

10. The method of claim 5, wherein BAIBA is administrated to promote the liver glycogen synthase activity and augment liver glycogen storage capability.

11. The method of claim 5, wherein BAIBA comprises L-BAIBA, D-BAIBA, or a combination thereof.

12. The method of claim 5, wherein BAIBA is administrated in a form of capsule, granule, powder, tablet, functionalized food, toothpaste, or sublingual articles.

13. The method of claim 1, wherein the predefined number of days include 14 days or less.

14. The method of claim 5, wherein the predefined number of days include 14 days or less.

* * * * *